United States Patent
Tribble et al.

(10) Patent No.: US 7,096,212 B2
(45) Date of Patent: Aug. 22, 2006

(54) SERIAL DATA CAPTURE AND PROCESSING

(75) Inventors: Dennis Tribble, Oklahoma City, OK (US); Joel A. Osborne, Oklahoma City, OK (US)

(73) Assignee: ForHealth Technologies, Inc., Daytona Beach, FL (US)

( * ) Notice: Subject to any disclaimer, the term of this patent is extended or adjusted under 35 U.S.C. 154(b) by 880 days.

(21) Appl. No.: 09/991,048

(22) Filed: Nov. 21, 2001

(65) Prior Publication Data

US 2003/0097368 A1 May 22, 2003

(51) Int. Cl.
*G06F 17/30* (2006.01)
(52) U.S. Cl. .................... 707/1; 707/3; 707/10
(58) Field of Classification Search .......... 707/3, 707/6, 1, 10; 705/2, 3; 235/375, 385; 600/300
See application file for complete search history.

(56) References Cited

U.S. PATENT DOCUMENTS

| | | | |
|---|---|---|---|
| 5,337,919 A * | 8/1994 | Spaulding et al. | 221/2 |
| 5,805,454 A | 9/1998 | Valerino, Sr. et al. | |
| 5,883,370 A * | 3/1999 | Walker et al. | 235/375 |
| 5,915,089 A | 6/1999 | Stevens et al. | |
| 6,048,086 A | 4/2000 | Valerino, Sr. | |
| 6,202,923 B1 * | 3/2001 | Boyer et al. | 235/375 |
| 6,226,745 B1 * | 5/2001 | Wiederhold | 707/9 |
| 2002/0188467 A1 * | 12/2002 | Eke | 705/2 |
| 2003/0033532 A1 * | 2/2003 | Marks | 713/182 |
| 2004/0088187 A1 * | 5/2004 | Chudy et al. | 705/2 |
| 2004/0236630 A1 * | 11/2004 | Kost et al. | 705/14 |

OTHER PUBLICATIONS

Ateniese et al. Anonymous E-Prescriptions, Workshop On Privacy In The Electronic Society, Proceeding of the 2002 ACM workshop on Privacy in the Electronic Society, 2002, pp. 19-31.*

* cited by examiner

*Primary Examiner*—Jean M. Corrielus
*Assistant Examiner*—Baoquoc N. To
(74) *Attorney, Agent, or Firm*—Darby & Darby

(57) ABSTRACT

A method and software interface enables serial data streams to be trapped, parsed, tested for suitability for automated handling by a medication preparation system. Only those portions of the serial data stream that are not suitable for such handling are released for printing and manual handling. A serial data interface includes a listener software module ("LSM") that receives serial data streams and a parser software module ("PSM") communicatively connectable to the LSM that processes the serial data streams received from the LSM. A set of configuration rules accessible by the PSM defines the manner of processing by the PSM on the serial data streams. A data structure results that enables data handling by an automated medication preparation system.

30 Claims, 3 Drawing Sheets

SERIAL DATA CAPTURE AND PROCESSING

FIELD OF THE INVENTION

The present invention relates to interfaces using serial printer emulators and, more specifically, to a serial data interface that permits data configuration and trapping.

BACKGROUND OF THE INVENTION

The task of integrating multiple systems into a computer network is often associated with custom programming and delays. This is particularly true when dealing with proprietary network components such as may often be found in hospital environments. For example, hospital information systems are conventionally employed to manage patient data and input medications that are to be administered to a patent. An electronic hospital information system typically must interact with an electronic pharmacy system within an automated facility, the interface between these two systems requires that the software communicate and process the data appropriately. When integrating a new network component into an existing system, the software providers of each system must meet and agree upon specifications prior to even establishing a project timetable, in order to ensure that the necessary communications and processing needs are met. This is attendant with great expense and difficulty.

On the other hand, most hospital information systems and pharmacy systems send data to label printers that identify a patient, a medication to be administered, the time of administration, contra-indications, and other data. It makes no difference whether the label printer is a local or network device. Thus, one way of obtaining a reliable data stream from one system for importing into another is to capture the data that is intended to be printed to a label. However, in order to operate on this data, subsequent processing is required. The present invention provides improvements in device interaction by initiating tasks in response to the receipt of data at a serial port that parse and manage the information in that data stream for handling by other network devices. In further aspects, the present invention identifies label data in a serial data stream and divides the label data into a first stream that launches automated medication preparation processes and a second stream that is redirected to a conventional printer.

SUMMARY OF THE INVENTION

In accordance with one aspect of the invention, a method for selectively trapping data streams intended for a pharmacy comprises the steps of: trapping a printer output stream of an order entry system; parsing the output stream for prescribed information; testing the parsed output stream against an order database to determine suitability for automated handling by a medication preparation system associated with the pharmacy; and releasing only those portions of the output stream that are not suitable, the released output stream being printed for manual handling.

In a particular embodiment of the invention, the foregoing method includes additional steps of populating a data structure with data parsed from the printer output stream in accordance with a set of configuration rules. In another embodiment, the printer output stream can identify its source so that the parsing step can parse the printer output stream in accordance with a set of configuration rules for that source.

In a particularly preferred embodiment, the printer output stream is saved as a record in a database. In this preferred method, metadata can be associated with the output stream to assist in further processing. Thus, for example, the metadata can identify the source of the printer output stream and include that source data for each record for use in parsing the printer output stream. The metadata can also include a marker indicative of whether a given record has been parsed, with the marker being used in database queries to locate a subset of records that have been marked as not yet having been parsed. The data in the record can be used to populate the data structure, as described above. It should be understood, however, that printer output streams and, more generally, serial data streams, can be mangaed by the methods of the present invention whether saved in a database or operated upon on the fly.

In accordance with another aspect of the present invention, a serial data interface is provided which comprises: at least one listener software module ("LSM") executing on a first machine, the LSM receiving serial data streams from a port of the first machine; a parser software module ("PSM") communicatively connectable to the LSM and executing on a second machine, the PSM processing the serial data streams received from the LSM to extract data therefrom and populate a data structure therewith; and a set of configuration rules accessable by the PSM, the set of configuration rules defining the manner of processing by the PSM on the serial data streams from a prescribed LSM, wherein the data structure enables data handling by an automated medication preparation system.

Depending on the complexity or needs of a given implementation, the PSM and LSM can execute on the same machine. In a preferred embodiment, the serial data stream identifies a particular LSM and the set of configuration rules used for processing the serial data stream is selected for the identified LSM. As in the method above, embodiments can save the received serial data streams as records in a database or operate on the data as it comes in over a port of the machine, and preferably utilize metadata of the type mentioned above and described more fully hereinbelow.

These and other aspects, features, steps and advantages can be appreciated further from the accompanying Drawing Figures and Detailed Description of Certain Embodiments.

BRIEF DESCRIPTION OF THE DRAWING FIGURES

DETAILED DESCRIPTION OF CERTAIN EMBODIMENTS

Figure 1:
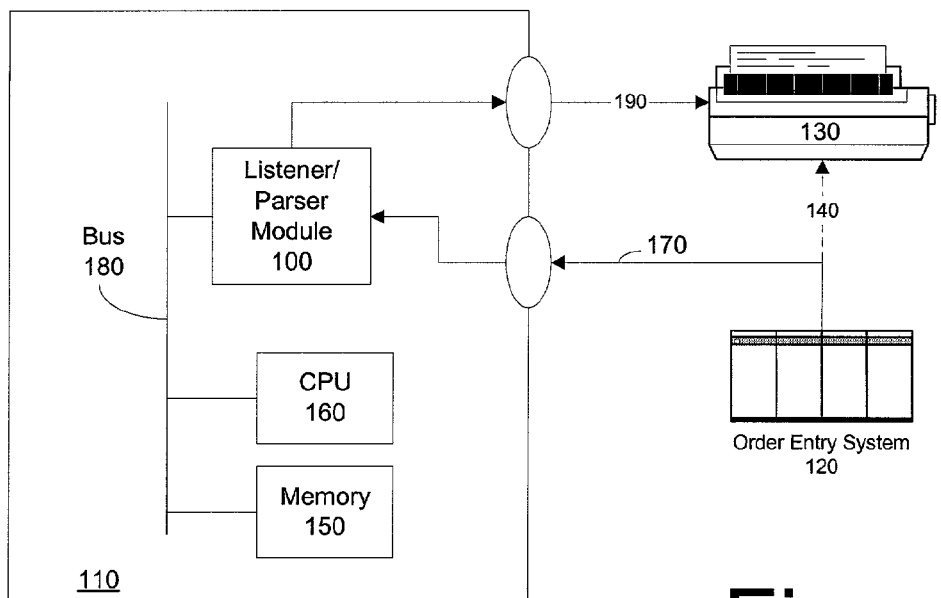
FIG. 1 is a functional block diagram of a software listener and parser module in accordance with an exemplary embodiment, and further illustrating its functional connections to a computer network.

By way of overview and introduction, the present invention provides a software interface that enables a network device to emulate a printer that is attached to a network serial port in order to trap and filter serial data for automated handling by downstream equipment. Externally, the interface exposes itself as a printer device that receives serial print strings, traps the data into a buffer or data store, parses the print string to extract data, and outputs the extracted data into a format usable by the network device. Preferably, the parsing routine is configurable to handle a variety of different data streams thereby permitting the interface to be used with standard networks and network devices without programming their respective output and input streams.

In a preferred implementation, the serial interface is used to bridge a hospital information system to an automated medication preparation station. The hospital information system, in response to operator input or a program resident in that system, generates a stream of output data preconfigured to print onto labels. Ordinarily, this output stream is directed to a printer in a local or on-premises pharmacy and is used to prepare medications. The label is thereafter applied to the preparation. The preferred embodiment of the invention provides a configuration routine that permits an installer to configure a set of rules by which a parser software module (described below) locates the start and end of the data for each label, as well as discrete data elements within the label data. The configuration routine thereby allows a user to configure messages that pass through the interface to be properly parsed for a given pharmacy system. Because users ordinarily can format labels for pharmacy systems as desired, both the structure of the incoming message to the pharmacy system and the rules for parsing these messages are field configurable, thereby providing great flexibility to the interface of the present invention.

In the preferred implementation, both the listener and the parser are included on the same machine within an automated medication operation system to provide an interface to an order entry system ("OES"). An exemplary automated medication operation is the PARxD IV medication preparation system of For Health Technologies, Inc., Oklahoma City, Okla., which prepares syringes for intravenous introduction. An exemplary OES is the PharmNet Millennium hospital information system of Cerner Corporation, of Kansas City, Mo. The PARxD IV is a software-controlled medical device that receives and manufactures orders for syringes for future (batch) or current (new order) production. The PARxD IV device contains knowledge about how the syringes are to be prepared (final dose volume, diluents, etc.) and so the incoming order from the OES need only specify the drug and dose to be delivered, the patient name, the location of the patient, and other administrative information that may be of use to have on the syringe label.

With reference now to FIG. 1, a functional block diagram of a software listener and parser module 100 is shown within an automated medication preparation system 110 that may be used within a pharmacy or other formulary. In conventional pharmacies in which the automated system 110 is not present, an OES 120 located somewhere in the building sends new and batch orders for drugs to a label printer 130 over a serial data communication connection 140. For example, the OES 120 has an RS-232 serial port for one-way data communication over the link 140 to a standard printer 130 fitted with paper or, more typically, adhesive labels. However, in accordance with the present invention, the automated system 110 is fitted with listener software, described below, that is preferably running resident in the automated system 110, for example by being loaded into a memory 150 and executed by a central processing unit ("CPU) 160. The automated system 110 is connected directly or through a computer network to the serial port of the OES 120 through a one-way communication connection 170. The listener module manages data received across the connection 170, for example, through a data bus 180 within the automated system 110. The serial data on connection 170, the CPU 160, the memory 150 and the listener module 100 are preferably all communicatively coupled to the data bus 180.

The arrangement of FIG. 1 provides a listener module and a parser module together at the automated system 110, but these modules can be resident in different machines, as described below in connection with the arrangement of FIG. 4. The parser module operates on the data received from the OES 120 to selectively cause the automated system 110 to manufacture drug dosages for administration to patients or to reject the data as not suitable for handling. Thus, depending on the configuration of the automated system 110, the parser can cause the automated system to prepare intravenous doses, oral doses, or doses suitable for specific therapies such as chemotherapy. Typically, the automated system 110 is configured to prepare only one of these dosages types and so any dosage form outside the system's configuration (e.g., tablets) is rejected as not being suitable for handling. Those drug orders that are not suitable are sent to the label printer 130 as a serial data output stream 190. Consequently, the listener/parser module 100 enables drug orders to be better managed, with those susceptible to automated preparation being prepared without user intervention and with only those drug orders that are not suitable for the automated system 110 being sent to the label printer. This arrangement thereby reduces the number of drug orders that require manual handling, determines which orders require manual handling, and provides a filtered output stream 190 at the label printer 130 consisting of only those jobs that require manual handling.

Figure 2:
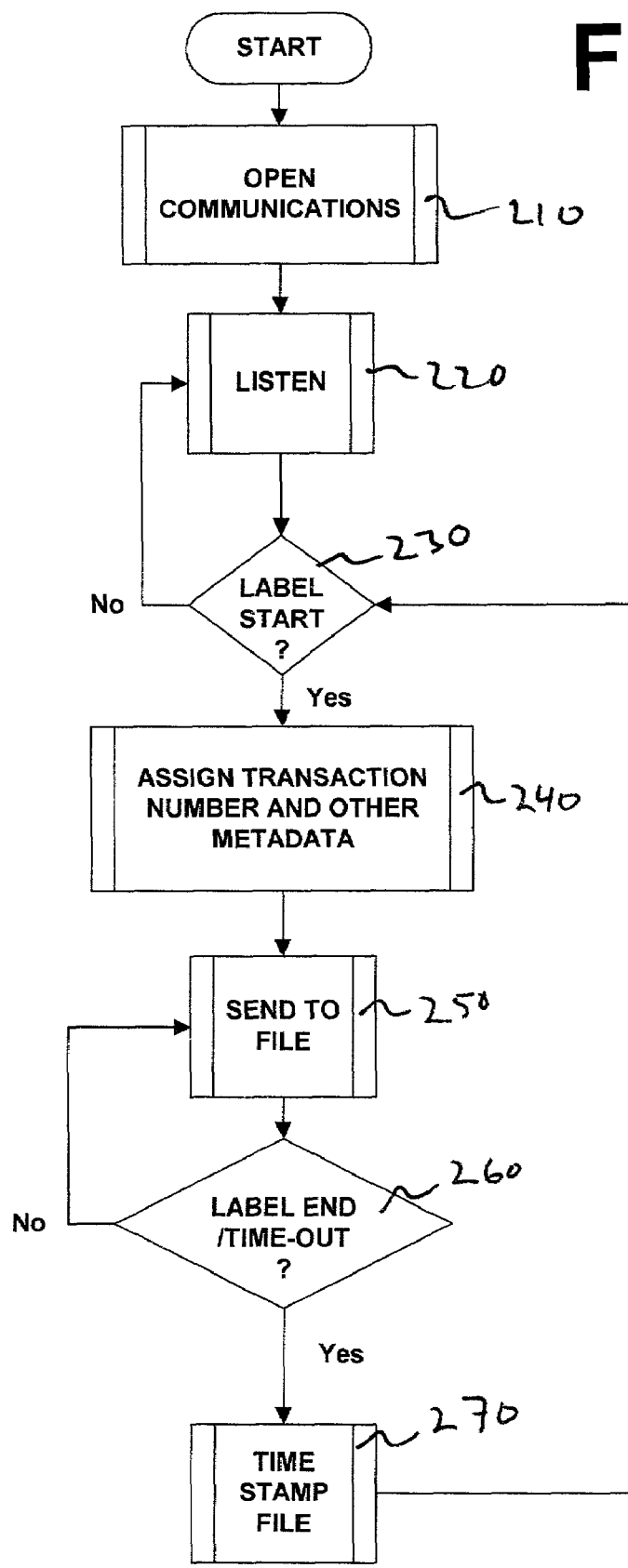
FIG. 2 is a flow diagram illustrating the operation of an exemplary embodiment of a listener software module (LSM).

The operation of the listener software module and the parser software module are described with reference to FIGS. 2 and 3, respectively.

The listener software module opens a serial communications channel on a serial port of the automated system 110 at step 210. For example, the listener module can be communicatively connected with the port making the connection 170 to the OES 120. Once communications have been opened, the listener software module (LSM) listens to that serial port for any data, at step 220. Preferably, drug orders are preceded by a character or character string that marks the beginning of a serial data stream. The LSM continuously tests to see whether a beginning-of-string character is detected at step 230, because such character or string denotes the start of label data. If a beginning character is not detected, then the LSM loops back to the listening step 220. On the other hand, if the start of a label is detected, then the serial data is written to a database together with (e.g., by appending) metadata.

As soon as the output stream is written to the database, the database assigns a unique transaction number, at step 240, to a newly opened log entry or record that will contain the incoming serial data. The LSM generates other data that is written to each log entry including the date and time of the transaction, the name assigned to the particular LSM that is writing the new database record, the serial data itself (sometimes referred to as "transaction text"), a marker to indicate whether the record requires parsing, a reference pointer that permits one database record to refer to another (e.g., for error checking purposes), and error condition information concerning errors that were observed on the communications line 170 during data transfer. This information is assigned to the transaction at step 240 as well. All of this information can be reviewed, if desired, using a viewer that displays each log entry together with any error messages that might have been generated or associated with a particular database record.

At step 250, the serial data itself is written to the record that was opened at step 240. The serial data continues to be written to that record until a label with an end-of-string character is detected or until a time-out event (e.g., end-of-message reached if no activity for X milliseconds) is detected, at step 260. Depending on the format of the data of received from the OES 120, there may or may not be an end of data stream character delimiting the end of a particular drug order. In the absence on the specific end-of-string delimiter, one drug order can be distinguished from the next either by detecting a beginning-of-string character or by permitting a prescribed time period to pass since the last data came in. Until an end-of-string condition is determined, the serial data continues to be sent to the database at step 250 and the end-of-string test at step 260 is repeated. When the end-of-string condition is determined, the record is time stamped at step 270 and the process flow loops back to step 230 to determine if a beginning-of-string character has been detected. As a result of the foregoing steps, records are created in the database by the LSM.

Figure 3:
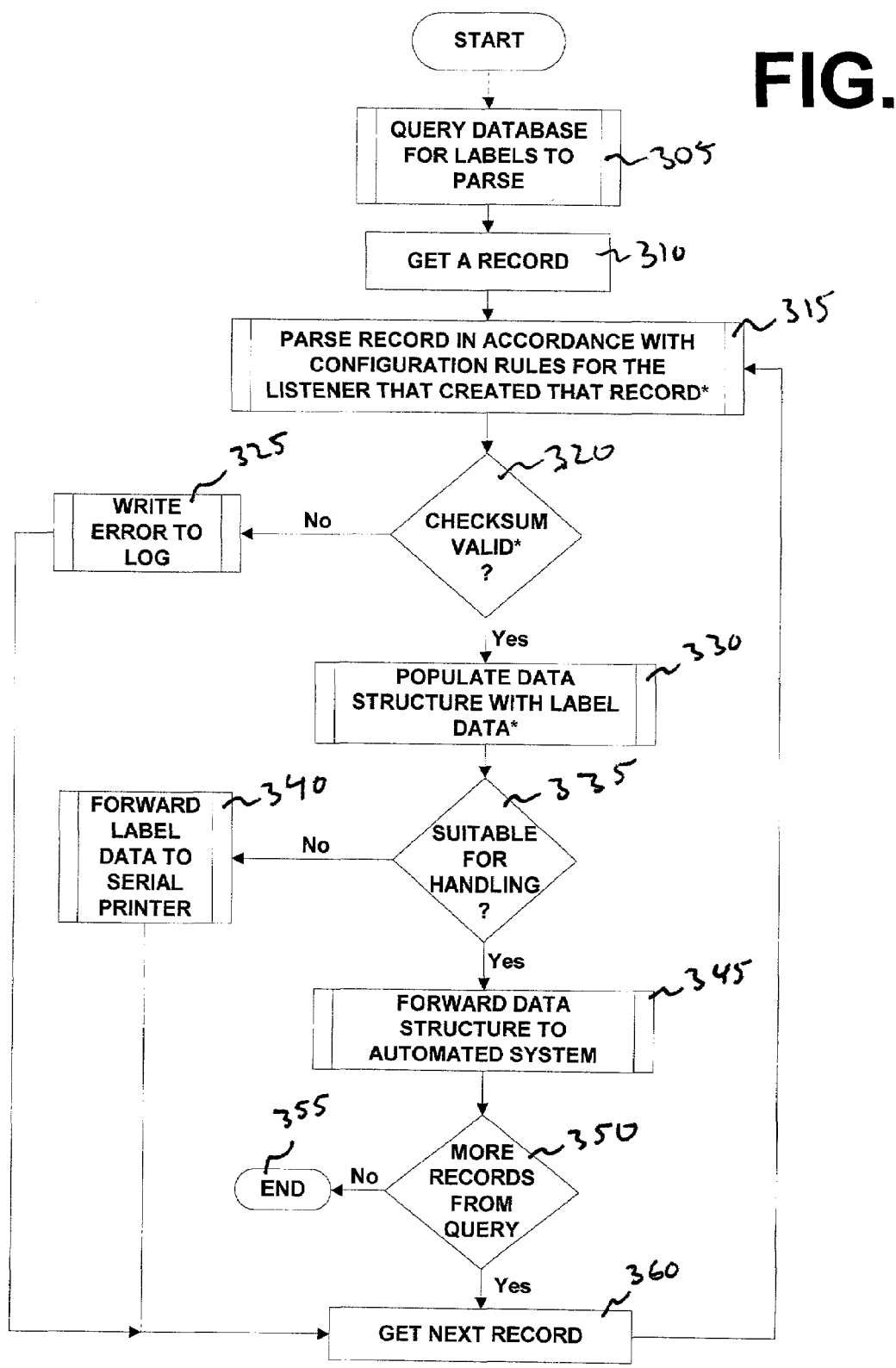
FIG. 3 is a flow diagram illustrating the operation of an exemplary embodiment of a parser software module (PSM).
Figure 1:
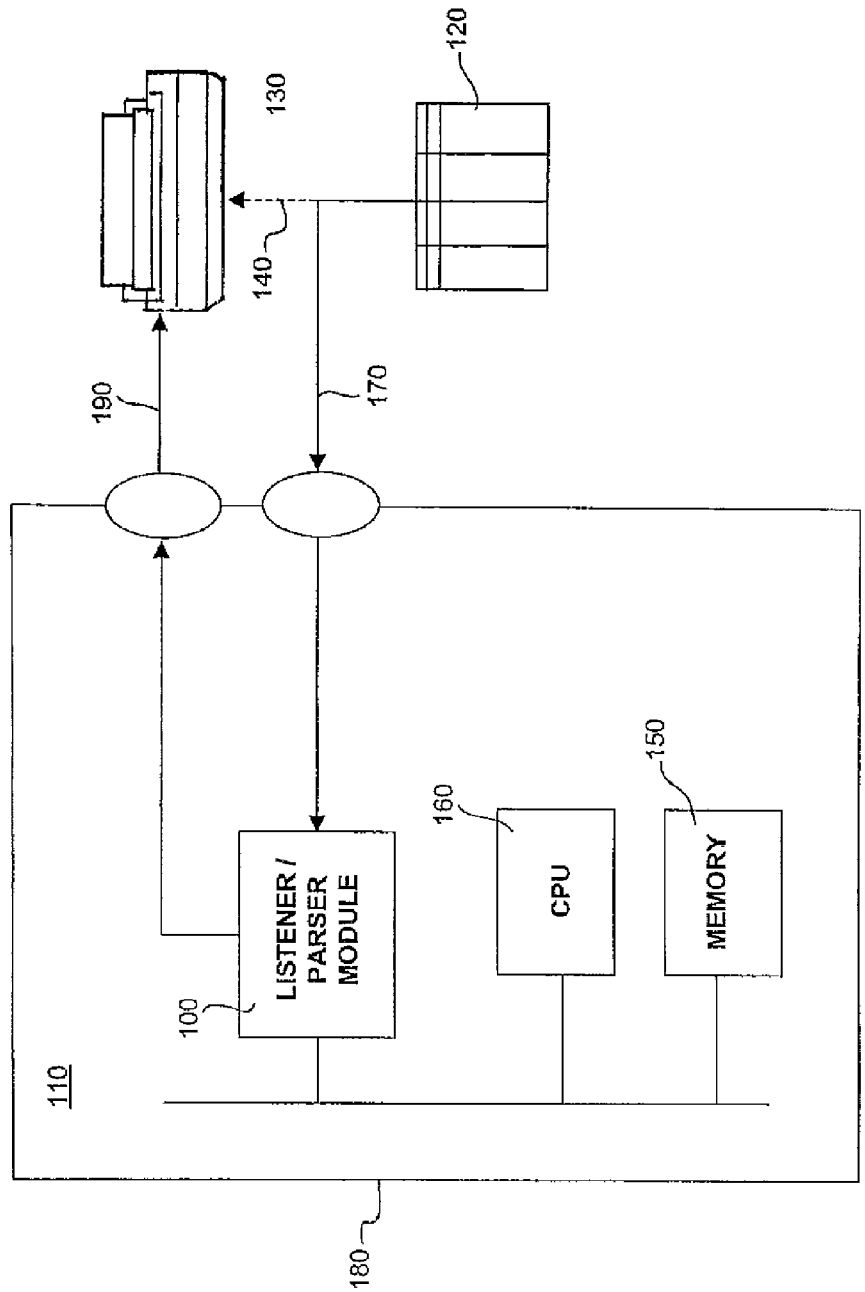
Figure 2:
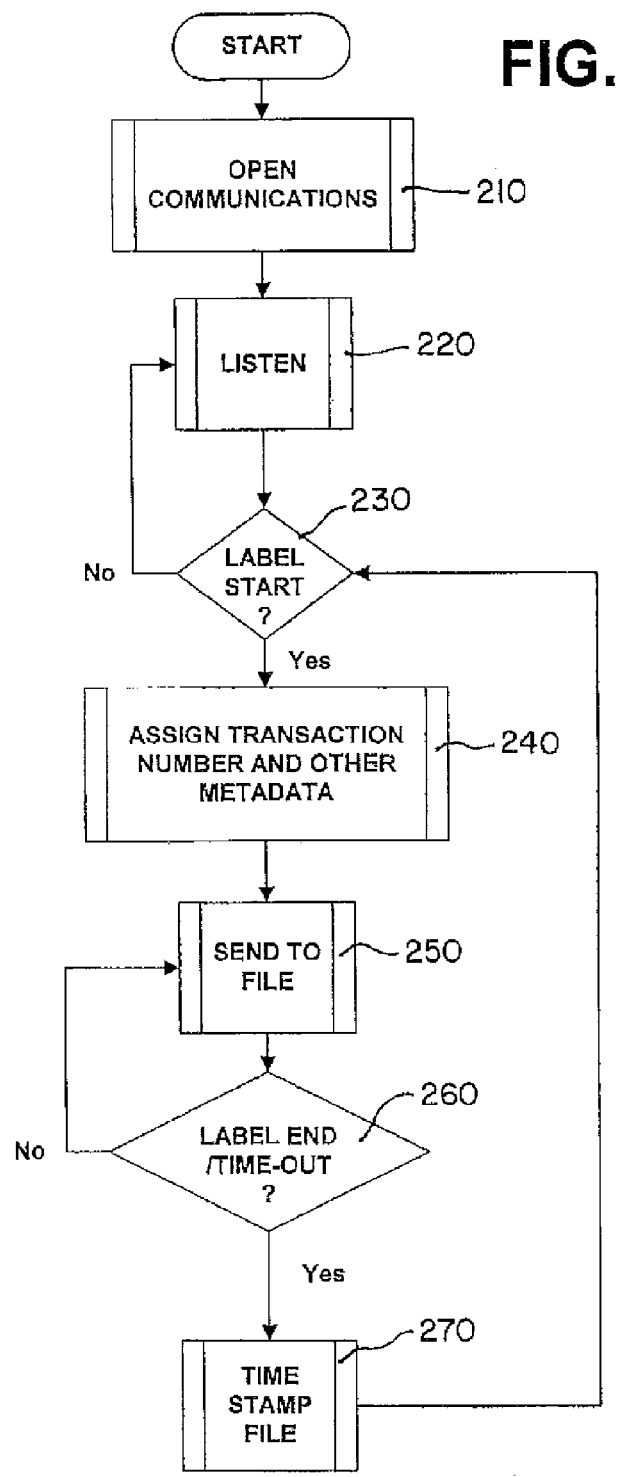
Figure 4:
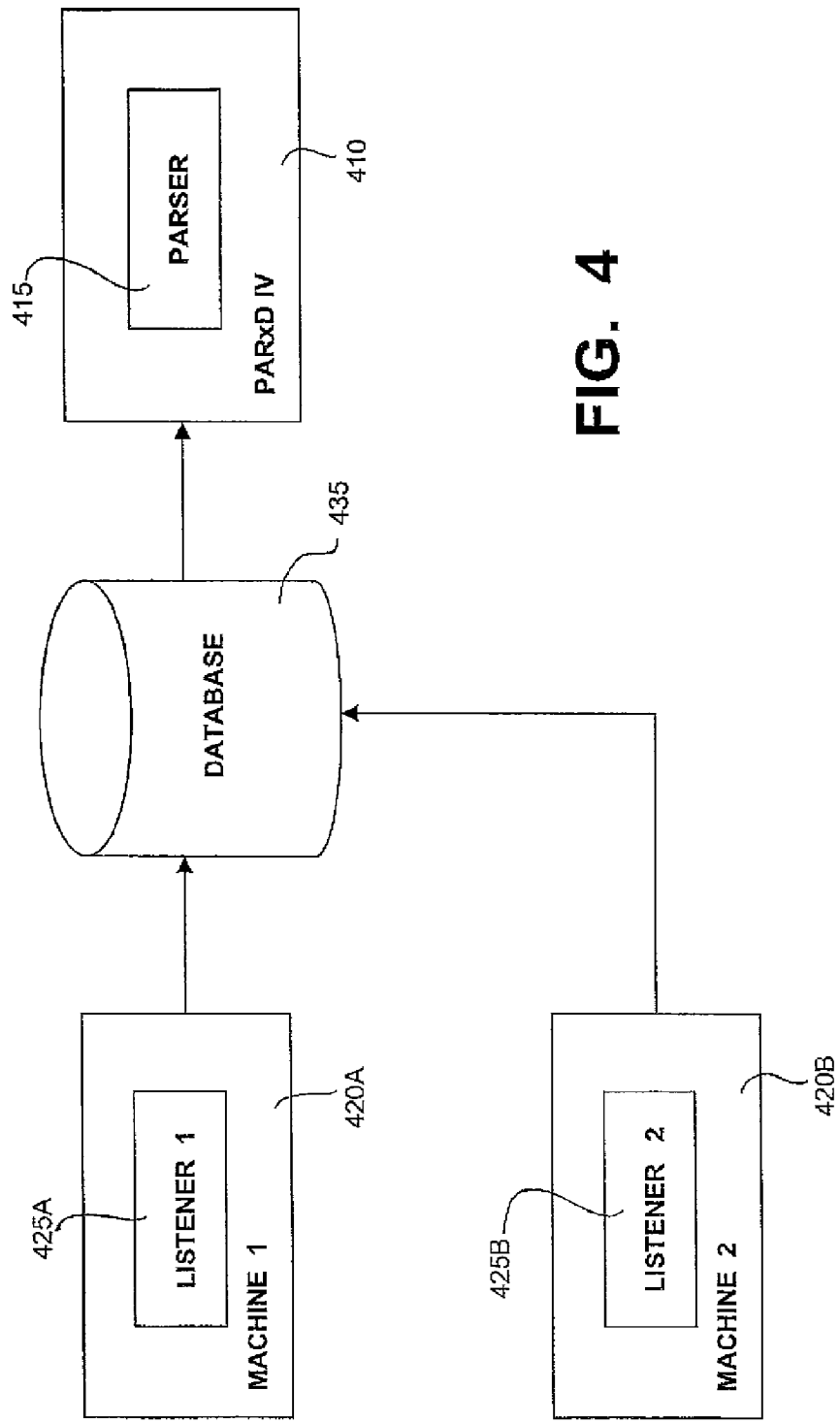

With reference now to FIG. 3, the operation of the parser software module (PSM) is described. At step 305, the PSM queries the database for any data that is to be parsed (i.e., data records that are marked as requiring parsing). As noted above, the LSM engrafts metadata to the serial stream coming into the automated system 110 over the connection 170. Part of the metadata includes a marker that tracks whether a given record has been parsed already (Parse="True") or not (Parse="False"). The marker can also be set to ensure that an error log entry is not parsed (by setting Parse to be "True" for that entry). The database query except 305 can take on a variety of forms, but generally selects all fields from the transaction log in which Parse="False." An index can be used to speed query processing, as understood by those of skill in the art. Essentially, the PSM uses the marker to determine which records have not been parsed, and returns a list of the labels that still must be parsed in order to fill all the drug orders (whether new or batch).

Using the returned list, a record is retrieved at step 310 and parsed by the PSM at step 315. Parsing is conducted in accordance with configuration rules that have previously been established for that LSM. The configuration rules can accommodate a variety of data formats including fixed formats, name-value pairs, and XML formats. For example, if the serial data is in a fixed format, then the drug order data will have prescribed positions within the serial data stream such as a patient name occupying character positions 15-45 on the fourth line of the label or positions 15–45 on the same line of the label as the word "patient." As another example, if the serial data is in the name—value pair format, the data may be located between a variable delimiter ("<Patient>") and an end-of-line character (e.g., CR, LF or both). Also, because the particular LSM is preferably identified in the data record, multiple data formats can be accommodated by the PSM and properly parsed by selecting a suitable set of configuration rules. A set of configuration rules, therefore, enables proper parsing of the data from the printer output stream into the data structure used by the PSM to determine suitability for handling and handling of drug orders by the automated medication preparation system.

Figure 4:
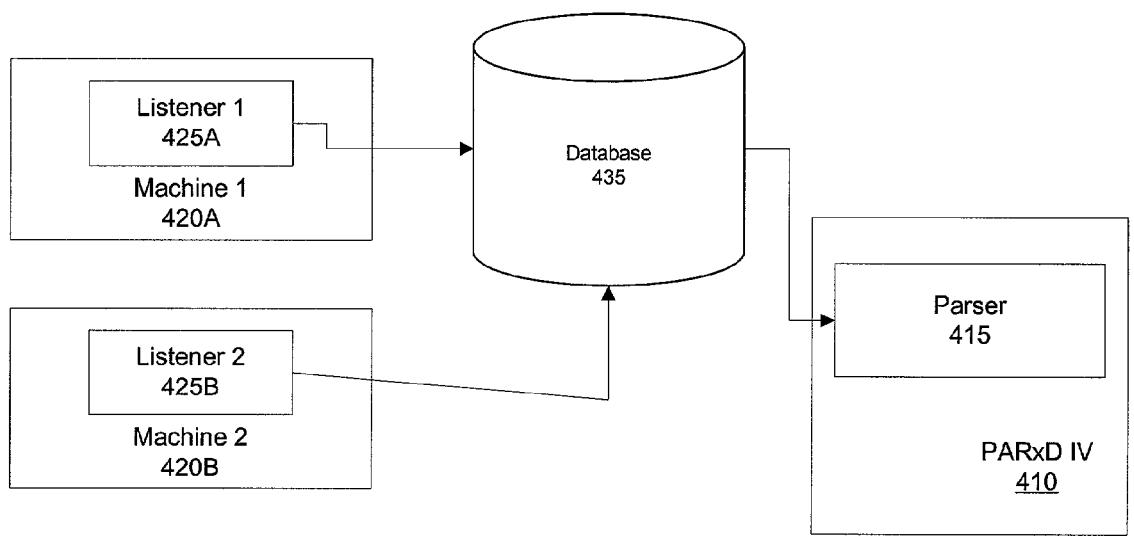
FIG. 4 is a distributed hardware arrangement in which the PSM is responsive to multiple LSMs.

With brief reference to FIG. 4, a distributed system 400 is illustrated in which the automated system 410 comprises the PARxD IV drug preparation system of For Health Technologies, Inc. The system 410 has a parser software module 415 executing as a resident software application on one machine. In this arrangement, there are two order entry systems, denoted 420A and 420B, comprising physically different machines than the one executing the PSM 415. The OESes 420A, 420B also comprise physically distinct systems, such as an inpatient system and an outpatient system configured to service different patient sets. Each OES has its own LSM 425A, 425B, respectively, which writes data records having uniquely assigned transaction numbers to a database 435. OES 425A and 425B can have different data formats, yet because each new data record identifies the source of the record (L1 or L2), the parser 415 can properly parse records as they are retrieved at step 315.

Continuing the discussion of FIG. 3, a test is made at step 320 to determine whether the data received from the OES was received correctly. For example, the test can ensure that the checksum was valid and check its type (Mod 43, 16-bit cycle redundancy check ("CRC"), 32 bit CRC, etc.). If the data entered into the data record did not write correctly, the error is written to the database at step 325, for example as a new log entry, and the next database record in the list is retrieved at step 360. The new log entry preferably includes a reference pointer back to the log entry that had the error.

On the other hand, if the checksum were valid, then the transaction data is populated into a data structure at step 330. The data structure is selected to be compatible with the automated system 110, 410 and serves to assign each of the required data values with a variable. The variables that are included in the data structure can include, but are not limited to: the patient's name, location within the hospital or other institution, a drug code (e.g., the national drug code ("NDC"), the drug named in the drug order, the dose, the units, the administration date, the administration time, the order date, the order time, the checksum, any label comments, the order type (e.g. batch or new), and order frequency (e.g. "q6h6," for every six hours starting at 6 A.M.).

With the serial data now contained in the data structure of the automated system 110, 410, the drug order is tested at step 335 by the parser to see whether it is suitable for handling by the automated system. A given drug order is generally suitable for handling unless one of the following limited circumstances exists:

1. The automated medication preparation system cannot recognize the drug code included in the drug order.
2. The automated medication preparation system recognizes the drug code but does not handle the drug in the drug order and therefore cannot fill the drug order.
3. The automated medication preparation system understands the drug code and ordinarily can fill the drug order, but does not have the required drug in stock at the present time.

Apart from these three circumstances, the test at step 335 should result in a determination that the drug order can be handled by the automated system. Preferably, the test for suitability for handling is made with reference to an order database that maintains tables of data concerning drug names and drug codes associated with those names in various dosages. In the event of the drug cannot be handled by the automated system, the next step 340 the drug order is forwarded to the label printer 130 for printing (e.g., onto an adhesive label) and manual handling by staff. If, however, the test that step 335 resulted in the determination that the drug order can be handled by the automated system, then the populated data structure is forwarded to the automated system for handling at step 345. In sophisticated applications, the data structure can first be routed to a scheduler for queue handling in accordance with a prescribed priority. For example, a new order can be processed ahead of a batch order if the prescribed priority is "whether time permits" such routing. It should be understood that the step of determining whether the drug order is suitable for handling results in the drug order being automatically processed or, if not automatically processed, a label being generated for only those drug orders that cannot be automatically processed. This results in proactive and dynamic filtering of drug orders as they come in over serial data lines from order entry systems, in view of the capabilities of the automated systems and their current stock of medications.

At step 350, a test is made to determine whether there are any more listed records to retrieve in response to the database query at step 305. If there are no more records to retrieve, the process ends at step 355. Otherwise, if there are more records, the next record is retrieved at step 360 and the process flow loops back to step 315 where the newly retrieved record is parsed in accordance with the configuration rules for the listener that created that record.

In operation, the PSM may return several different errors, each of which is preferably recorded as a log entry in the database. In the process flow of FIG. 3, steps 315, 320, and 330 are marked with an asterisk ("*") to indicate the steps at which errors might be returned. In particular, if data is missing that was expected to be included in the transaction data or that was to be provided by the LSM, an error code could result at step 315. If the checksum test at step 320 determines that the checksum is missing or does not match, an error code results and is written to the error log at step 325. Also, if required data is missing, the parser will determine this when populating the data structure with the transaction data, at step 330. Other errors can result which are not specifically noted above concerning interactions between the parser and one or more automated systems. A reference pointer to the problematic data record is preferably included whenever appropriate. A reference pointer is not appropriate, for example, when the error concerns a failure of the serial port or other hardware error.

It should be understood that the one-way serial listener interface lacks handshaking to permit confirmation that all information has been received intact from the OES. A more robust protocol such as HL7 over TCP/IP using a minimal lower layer protocol can be used, if necessary, to provide such confirmations.

The LSM is designed to trap a serial output stream of the type that is ordinarily sent to a label printer. This output stream is in the clear, that is, is non-proprietary, and includes critical information for preparing a medication. Thus, by trapping the output stream ordinarily intended for a label printer, the automated system can ensures compatibility with any hospital information system.

While the invention has been described in detail with particular reference to certain embodiments thereof, the invention is capable of other and different embodiments, and its details are capable of modifications in various obvious respects. As would be readily apparent to those skilled in the art, variations and modifications can be affected while remaining within the spirit and scope of the invention. Accordingly, the foregoing disclosure, description, and Drawing Figures are for illustrative purposes only, and do not in any way limit the invention, which is defined only by the claims.

We claim:

1. A computer-implemented method for selectively trapping output streams containing one or more medication data intended for a pharmacy, comprising the steps of:
    (A) trapping a printer output stream of an order entry system, the printer output stream identifying a source of the printer output stream;
    (B) parsing the output stream for prescribed information in accordance with a set of configuration rules associated with the source;
    (C) testing the parsed output stream against an order database to determine suitability of the medication data therein for automated handling by a medication preparation system associated with the pharmacy;
    (D) using the medication preparation system, preparing one or more medications corresponding to the one or more medication data determined to be suitable;
    (E) releasing only those portions of the output stream that are not suitable, the released output stream being printed for manual handling; and
    (F) population a data structure with data parsed from the printer output stream in accordance with the set of configuration rules.

2. The method of claim 1, including the additional step of populating a data structure with data parsed from the printer output stream in accordance with a set of configuration rules.

3. The method of claim 1, wherein the printer output stream identifies a particular listener software module ("LSM").

4. The method of claim 3, wherein the source is the particular LSM and wherein the step of populating the data structure with data parsed from the printer output stream in accordance with the set of configuration rules for the particular LSM.

5. The method of claim 3, wherein the parsing step further comprises testing the output stream for a beginning of serial data stream character.

6. The method of claim 1, wherein the trapping step comprises saving the output stream as a record in a database.

7. The method of claim 6, including the additional step of associating metadata with the output stream.

8. The method of claim 7, wherein the printer output stream is from a listener software module ("LSM") and the metadata for each record identifies the trapped printer output stream as being from that said LSM.

9. The method of claim 7, wherein the metadata includes a marker indicative of whether a given record has been parsed.

10. The method of claim 9, including the additional step of querying the database to identify a subset of records marked as not having been parsed.

11. The method of claim 10, wherein the parsing step includes the steps of:
    (A) retrieving the subset of records; and
    (B) parsing the subset of records in accordance with a set of configuration rules.

12. The method of claim 11, including the additional step of populating a data structure with data parsed from each retrieved record in accordance with the set of configuration rules.

13. The method of claim 11, wherein the printer output stream is from a listener software module ("LSM"), the metadata for each record identifies the trapped printer output stream as being from that said LSM, and the set of configuration rules is prescribed for that said LSM.

14. The method of claim 13, including the additional step of populating a data structure with data parsed from each retrieved record in accordance with the set of configuration rules.

15. The method of claim 1, including the additional step of printing the released output stream onto an adhesive label.

16. The method of claim 1, wherein the testing step comprises testing whether the printer output stream was trapped correctly.

17. The method of claim 16, wherein the testing step performs a checksum test on the printer output stream.

18. The method of claim 1, wherein the printer output stream of the order entry system includes a drug order and wherein the drug order fails the testing step as not suitable for automated handling by the medication preparation system under one or more of the following conditions:
  1. the automated medication preparation system cannot recognize a drug code included in the drug order;
  2. the automated medication preparation system recognizes the drug code but does not handle the drug specified in the drug order and therefore cannot fill the drug order;
  3. The automated medication preparation system recognizes the drug code and ordinarily can fill the drug order, but does not have the required drug in stock at the present time.

19. The method of claim 1, including the additional step of routing a suitable order to a scheduler for handling in accordance with a prescribed priority.

20. A computer system including software loaded into a memory of one or more machines executable by one or more processors to support of serial data stream management, comprising:
  (a) at least one listener software module ("LSM") executing on a first machine, the LSM receiving serial data streams containing one or more medication data from a port of the first machine;
  (b) a parser software module ("PSM") communicatively connectable to the LSM and executing on a second machine, the PSM processing the serial data streams received from the LSM to extract the one or more medication data therefrom and populate a data structure therewith; and
  (c) a set of configuration rules accessible by the PSM, the set of configuration rules defining the manner of processing by the PSM on the serial data streams from a prescribed LSM,
  wherein the PSM is configured to determine suitability for handling of drug order by an automated medication preparation system with reference to an order database, and
  wherein the data structure enables data handling and preparation of one or more medications by an automated medication preparation system.

21. The interface of claim 20, wherein the PSM communicates with only one LSM.

22. The interface of claim 20, wherein the first and second machines are the same machine.

23. The interface of claim 20, wherein the serial data stream identifies a particular LSM and wherein the set of configuration rules used for processing the serial data stream by the PSM is selected for the identified LSM.

24. The interface of claim 20, wherein the LSM saves the received serial data streams as a record in a database.

25. The interface of claim 24, wherein the LSM associates metadata with the received serial data streams.

26. The interface of claim 25, wherein the metadata includes a marker indicative of whether a given record has been parsed.

27. The interface of claim 26, wherein the PSM is configured to query the database and identify a subset of records marked as not having been parsed.

28. The interface of claim 27, wherein the PSM is further configured to retrieve the subset of records and parse the subset of records in accordance with the set of configuration rules.

29. The interface of claim 28, wherein the processing by the PSM includes selectively printing portions of the received serial data stream onto an adhesive label.

30. The interface of claim 20, wherein the PSM is configured to route the data in the populated data structure to a scheduler for handling in accordance with a prescribed priority.

* * * * *

(12) INTER PARTES REEXAMINATION CERTIFICATE (1196th)
United States Patent
Tribble et al.

(10) Number: US 7,096,212 C1
(45) Certificate Issued: Oct. 27, 2015

(54) SERIAL DATA CAPTURE AND PROCESSING

(75) Inventors: Dennis Tribble, Oklahoma City, OK (US); Joel A. Osborne, Oklahoma City, OK (US)

(73) Assignee: BAXTER CORPORATION ENGLEWOOD

Reexamination Request:
No. 95/000,333, Jan. 18, 2008

Reexamination Certificate for:
Patent No.: 7,096,212
Issued: Aug. 22, 2006
Appl. No.: 09/991,048
Filed: Nov. 21, 2001

(51) Int. Cl.
*G06F 17/30* (2006.01)
*G06F 19/00* (2011.01)

(52) U.S. Cl.
CPC .... *G06F 17/30592* (2013.01); *G06F 17/30575* (2013.01); *G06F 19/3406* (2013.01); *G06F 19/3456* (2013.01)

(58) Field of Classification Search
None
See application file for complete search history.

(56) References Cited

To view the complete listing of prior art documents cited during the proceeding for Reexamination Control Number 95/000,333, please refer to the USPTO's public Patent Application Information Retrieval (PAIR) system under the Display References tab.

*Primary Examiner* — Christopher E. Lee

(57) ABSTRACT

A method and software interface enables serial data streams to be trapped, parsed, tested for suitability for automated handling by a medication preparation system. Only those portions of the serial data stream that are not suitable for such handling are released for printing and manual handling. A serial data interface includes a listener software module ("LSM") that receives serial data streams and a parser software module ("PSM") communicatively connectable to the LSM that processes the serial data streams received from the LSM. A set of configuration rules accessible by the PSM defines the manner of processing by the PSM on the serial data streams. A data structure results that enables data handling by an automated medication preparation system.

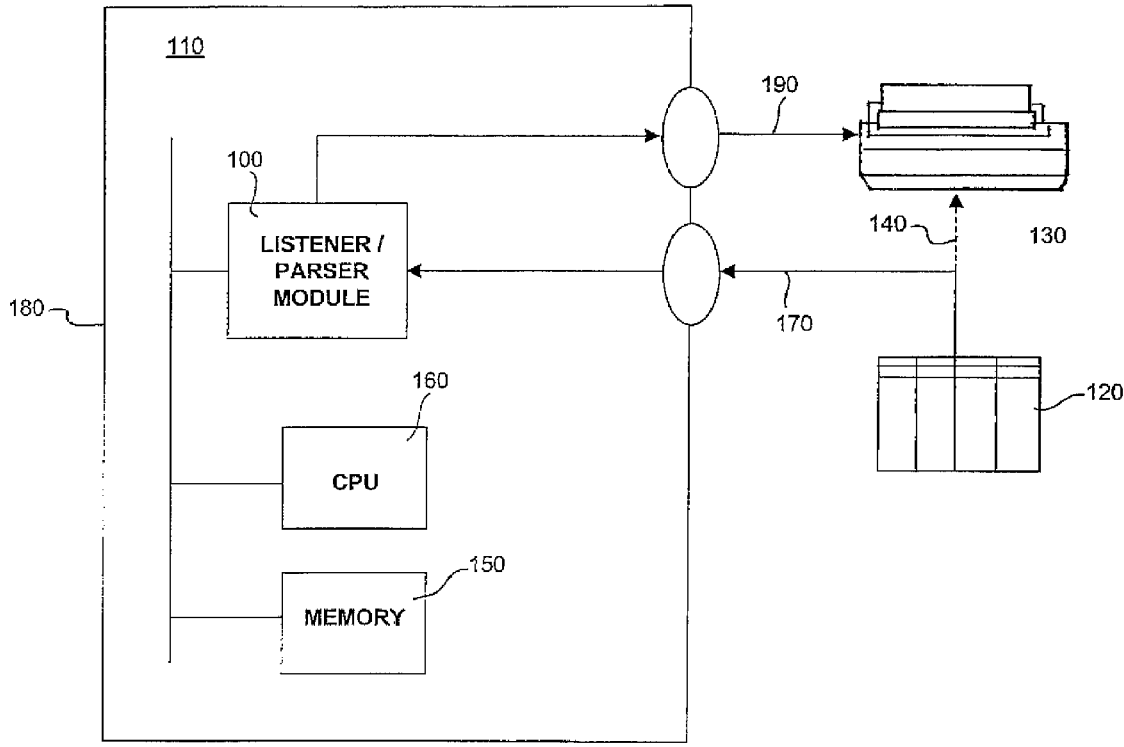

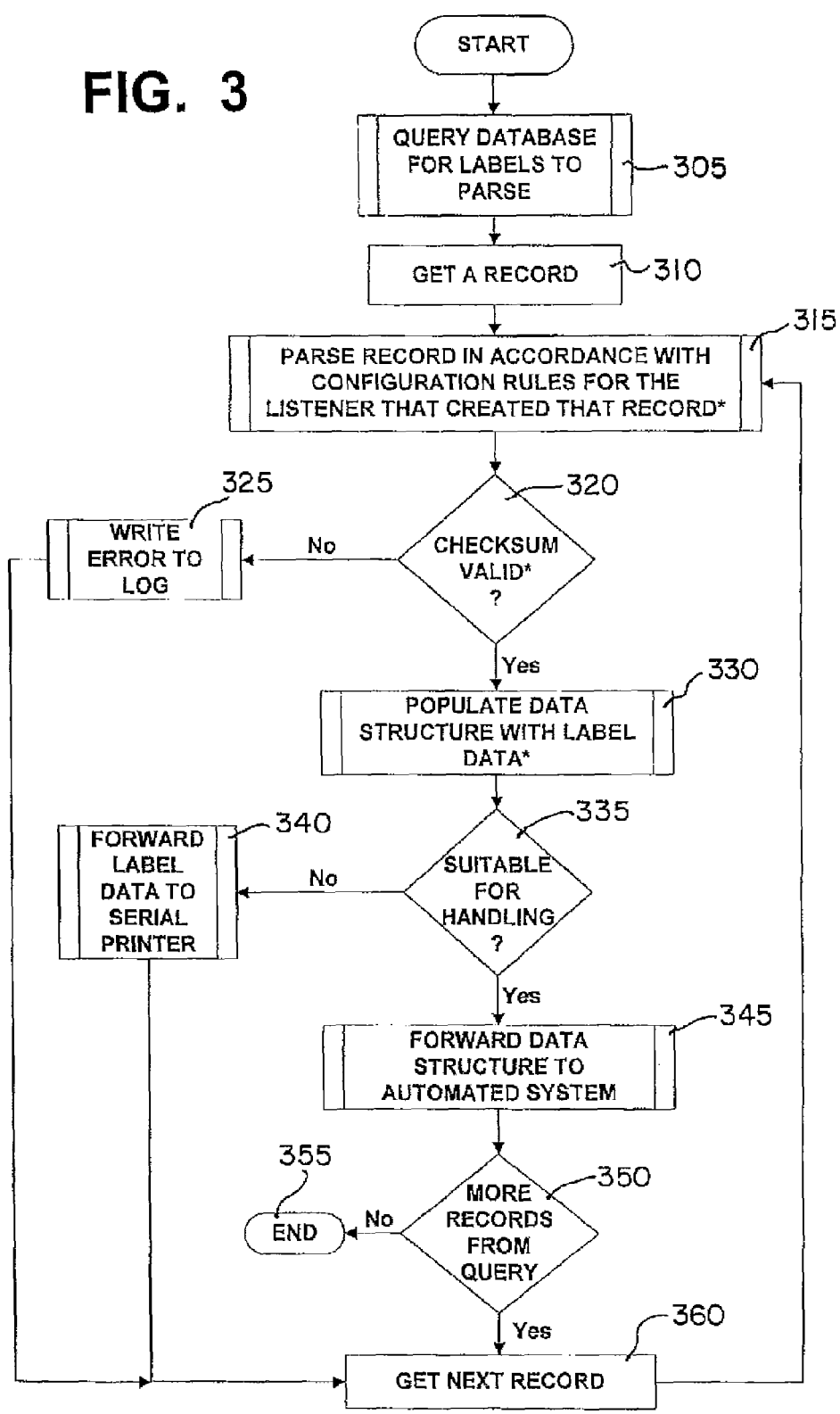

INTER PARTES REEXAMINATION CERTIFICATE

THE PATENT IS HEREBY AMENDED AS INDICATED BELOW.

THE DRAWING FIGURES HAVE BEEN CHANGED AS FOLLOWS:

Substitute sheets 1-4 replace the drawings of the patent. The substitute sheets render FIGS. 1 and 2 on separate sheets whereas the patent had them depicted on the same sheet. The substitute sheets replace the hand-drawn reference numbers with typed reference numbers.

AS A RESULT OF REEXAMINATION, IT HAS BEEN DETERMINED THAT:

Claims 1-30 are cancelled.

\* \* \* \* \*